United States Patent [19]
Nakanishi et al.

[11] Patent Number: 6,025,513
[45] Date of Patent: Feb. 15, 2000

[54] PREPARATION OF ALKYLHALOSILANES

[75] Inventors: Tetsuo Nakanishi; Tetsuya Inukai, both of Usui-gun; Kazumasa Tsukioka, Annaka; Hiroshi Nakayama, Annaka; Yukinori Satoh, Annaka, all of Japan

[73] Assignee: Shin-Etsu Chemical Co., Ltd., Tokyo, Japan

[21] Appl. No.: 09/106,145

[22] Filed: Jun. 29, 1998

[30] Foreign Application Priority Data

Jun. 27, 1997 [JP] Japan ................................. 9-187574

[51] Int. Cl.⁷ ........................................................ C07F 7/16
[52] U.S. Cl. ................................................................ 556/472
[58] Field of Search ............................................. 556/472

[56] References Cited

U.S. PATENT DOCUMENTS 4,864,044  9/1989  Lewis et al. .............................. 556/472

*Primary Examiner*—Paul F. Shaver
*Attorney, Agent, or Firm*—Millen, White, Zelano & Branigan, P.C.

[57] ABSTRACT

An alkylhalosilane is prepared by charging a reactor with a contact mass comprising a metallic silicon powder and a copper catalyst, and feeding an alkyl halide into the reactor whereby the silane is formed by direct synthesis. The contact mass contains 1–10,000 ppm of elemental boron. The addition of boron to the contact mass is effective for increasing the throughput of dialkyldihalosilane at desired STY in an inexpensive manner while suppressing formation of unnecessary hydrosilanes and disilanes.

17 Claims, No Drawings

PREPARATION OF ALKYLHALOSILANES

BACKGROUND OF THE INVENTION

1. Field of the Invention

This invention relates to a process for preparing an alkylhalosilane by direct synthesis, and more particularly to a continuous process for preparing an alkylhalosilane by effecting gas-solid contact reaction between metallic silicon and alkyl halide in the presence of a copper catalyst.

2. Prior Art

With respect to the synthesis of alkylhalosilanes, Rochow first disclosed in U.S. Pat. No. 2,380,995 direct synthesis reaction between metallic silicon and an alkyl halide in the presence of a copper catalyst. Since then, there have been reported a number of research works relating to various co-catalysts used together with copper catalysts, various copper catalysts and treatment thereof, reactors, additives used during reaction, and the like.

The direct synthesis process involves activating a contact mass comprising metallic silicon and a copper catalyst, and introducing an alkyl halide into the activated contact mass for accomplishing gas-solid direct contact between metallic silicon and alkyl halide, thereby producing alkylhalosilanes.

In the industrial synthesis of alkylhalosilanes, the selectivity of dialkyldihalosilane and the formation rate of silanes are crucial because the dialkyldihalosilane is used most often in silicone resins. The selectivity of dialkyldihalosilane is evaluated in terms of a weight or molar ratio of dialkyldihalosilane to the silanes produced and a T/D ratio. Alkylhalosilane products contain dialkyldihalosilane (D), trialkylhalosilane (M), alkyltrihalosilane (T), etc. as well as other by-products such as alkylhydrodihalosilane (H) and alkylhalodisilane. In particular, disilanes are known as a residue or waste among silane manufacturers because few processes are available for the effective utilization of disilanes, and most disilanes are discarded. The T/D ratio is a compositional ratio of alkyltrihalosilane to dialkyldihalosilane in the entire alkylhalosilanes produced, with a lower T/D ratio being preferred. The formation rate of alkylhalosilane is represented by a space time yield (STY) which is the weight of crude alkylhalosilanes produced per unit time relative to the weight of metallic silicon held in the reactor. In order to improve the content of dialkyldihalosilane produced, reduce the T/D ratio or increase the STY, various research works have been made with a focus on the catalyst and accelerator.

USSR Application Specification No. 617,569 (Certificate of inventorship No. 122,749) dated Jan. 24, 1995 discloses reaction in the presence of a metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 92421/1994 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated Jun. 2, 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122, 749). Also USSR Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 51596/1993 discloses that 25 to 2,500 ppm of a phosphorus compound capable of generating elemental phosphorus in the reactor is added to a contact mass.

For improving the direct synthesis of alkylhalosilanes, a number of researchers have made investigations on various metal co-catalysts. There is a desire to have more effective co-catalysts.

SUMMARY OF THE INVENTION

Therefore, an object of the present invention is to provide a process for preparing alkylhalosilane by direct synthesis, the process being capable of increasing the amount of dialkyldihalosilane produced in a desired STY while minimizing the amount of unnecessary hydrosilanes and disilanes.

The present invention pertains to the preparation of an alkylhalosilane by the commercially advantageous direct process, especially a direct alkylhalosilane preparing process capable of increasing the amount of dialkyldihalosilane produced in a desired STY while minimizing the amount of unnecessary hydrosilanes and disilanes. We have found that by adding boron to a contact mass comprising metallic silicon, formation of hydrosilanes and disilanes can be controlled while maintaining reactivity. Then the amount of dialkyldihalosilane produced can be increased. The present invention is predicated on this finding.

Although a variety of co-catalysts have been investigated as previously described, few reports have been made on boron compounds in which the invention is interested. For example, J. K. Tuset, Int. Sem. on Refining and Alloying of Liquid Al & Ferroalloys (1985), Trondheim describes that standard metallic silicon has a boron concentration of 50 ppm at most and that metallic silicon which has been purified for use in the direct synthesis has a boron concentration of 40 ppm at most. In many general descriptions, boron is regarded-as having little or no reactivity in the direct synthesis and when used in large amounts, becoming a catalyst poison. The boron concentration in metallic silicon used in practice largely varies among districts where silica rocks as the origin are mined. The boron concentration is originally low and further reduced in the step of refining to metallic silicon. Most contact masses are substantially free of boron. By our analysis, most metallic silicon powders refined from ores mined in South America, China and Australia have a boron concentration of less than about 10 ppm, and most metallic silicon powders refined from ores mined in Europe have a boron concentration of about 10 to about 30 ppm.

Against the general belief in the prior art that boron becomes a catalyst poison, we have found that boron is effective as a co-catalyst and that the addition of boron to the contact mass is effective for suppressing formation of unnecessary hydrosilanes and disilanes while maintaining reactivity, thereby increasing the throughput of dialkyldihalosilane.

The invention provides a process for preparing an alkylhalosilane of the general formula (1):

$$R_nSiX_{4-n} \quad (1)$$

wherein R is an alkyl group having 1 to 4 carbon atoms, X is a halogen atom, and letter n is an integer of 0 to 4, comprising the steps of charging a reactor with a contact mass comprising a metallic silicon powder and a copper catalyst, and feeding a reactant gas containing an alkyl halide into the reactor whereby the silane is formed by direct synthesis. According to the feature of the invention, the contact mass contains 1 to 10,000 ppm of elemental boron.

DETAILED DESCRIPTION OF THE INVENTION

Briefly stated, the process of the present invention is to prepare an alkylhalosilane through direct synthesis from metallic silicon powder and an alkyl halide in the presence of a copper catalyst.

The metallic silicon used herein should preferably have a purity of at least 97% by weight, especially at least 98% by weight. Preferred is metallic silicon powder obtained by pulverizing metallic silicon to an appropriate particle size. Where the reactor used is a fluidized bed reactor or agitation reactor, metallic silicon powder having a particle size of 5 to 150 μm is preferred in order that the metallic silicon powder be appropriately free fluidizing in the reactor. Note that the term "particle size" used herein is a particle size corresponding to 50% of a mass base cumulative oversize distribution curve by sieve analysis.

For the copper catalyst, any form of copper may be used, for example, elemental copper such as copper powder and stamped copper and copper compounds such as cuprous oxide, cupric oxide, and copper halides. An accelerator such as zinc, tin, antimony, and arsenic may be used as a co-catalyst. These accelerators may be used separately or as an alloy with copper. Exemplary accelerators are metallic zinc, tin, antimony, and arsenic powders, chlorides and oxides of zinc, tin, antimony, and arsenic, and copper alloys such as Cu—Zn, Cu—Sn, and Cu—Zn—Sn or variants thereof wherein Sb or As is used instead of Zn or Sn. The copper catalyst may be loaded in the reactor alone or as an alloy together with metallic silicon powder. The loading of the copper catalyst is preferably about 0.1 to 10 parts, especially about 2 to 8 parts by weight of copper per 100 parts by weight of the metallic silicon powder. When the co-catalyst is used, the loading of zinc is preferably 0.05 to 1 part by weight per 100 parts by weight of the metallic silicon powder, and the loading of tin, antimony and arsenic alone or in admixture is preferably 0.001 to 0.05 part, especially 0.005 to 0.01 part by weight per 100 parts by weight of the metallic silicon powder.

According to the feature of the invention, the contact mass used herein contains 1 to 10,000 parts by weight of elemental boron per million parts by weight of the contact mass (ppm, hereinafter). The contact mass preferably contains 5 to 10,000 ppm, more preferably 50 to 8,000 ppm, further preferably 55 to 6,000 ppm, and most preferably 200 to 5,000 ppm of boron.

In order that boron be present in the contact mass in the above-defined concentration, several procedures may be taken. For example, metallic silicon having a high boron concentration is used as the metallic silicon to construct the contact mass. In another procedure, a boron compound which volatilizes little at the melting temperature of metallic silicon is added during the preparation of metallic silicon, whereby metallic silicon having a high boron concentration is obtained. Alternatively, a boron compound is added to the reaction contact mass in the direct synthesis reactor.

Metallic silicon containing boron is obtainable by supplying a boron compound to silicon during a process involving the step of purifying silicon raw material. More particularly, in a process involving a silicon refining step, a non-volatile boron compound is added to silicon in a molten state. Examples of the boron compound used herein include naturally occurring minerals containing boron such as borax ($Na_2B_4O_7 \cdot 10H_2O$), kernite ($Na_2B_4O_7 \cdot 14H_2O$), and colemanite ($Ca_2B_6O_{11} \cdot 5H_2O$); borides represented by $M^1_2B$ where $M^1$ is Fe, Co, Ni, Mn, Mo, W, Ta or the like, $M^2_3B_2$ wherein $M^2$ is Mg or the like, $M_3B$ wherein $M^3$ is Fe, Co, Ni, Mn, Cr, Mo, W, Nb, Ta or the like, $M^4_3B_4$ wherein $M^4$ is Ta, Nb, Mn, Cr or the like, $M^5B_2$ wherein $M^5$ is Ti, Zr, Hf, V, Nb, Ta, Cr or the like, and $M^6_2B$, wherein $M^6$ is Mo, W or the like; boron nitride, boron carbide, boron phosphide, and boron phosphates. It is also preferable to use silicon having boron contained therein which is obtained by adding a boron compound under silicon refining conditions whereby the boron compound is reduced. The boron compounds to be added are boric acid, metal borates, and boron oxide. It is also acceptable to use boron compounds in gas phase or which readily volatilize.

Another procedure of containing boron in silicon is to use boron-containing quartz, boron-containing coal, boron-containing cokes, boron-containing char coal or boron-containing eucalyptus as the raw material to be refined into silicon. It is also possible to use boron-containing carbon as the electrodes for silicon refinement.

In the other procedure of adding a boron compound to the reaction contact mass, examples of the boron compound include elemental boron such as amorphous boron obtained by reducing oxides, boron-copper alloys, borides represented by $M^1_2B$, $M^2_3B_2$, $M^3B$, $M^4_3B_4$, $M^5B_2$, and $M^6_2B_5$ as defined above, boron nitride, boron carbide, boron phosphide, and boron phosphates. Since these boron compounds generally contain a trace amount of water, it is preferred that the boron compound is previously heat treated at about 200° C. in order to remove water before the boron compound is added to the direct synthesis reactor. Boron halides and other boron compounds in gas phase or which readily volatilize may also be used.

Alkyl halides are reacted with metallic silicon to form alkylhalosilanes. Exemplary alkyl halides include methyl chloride, ethyl chloride, propyl chloride, methyl bromide, and ethyl bromide. Among these, methyl chloride is commercially most useful. Dimethyldichlorosilane prepared using methyl chloride finds numerous applications as a raw material for a variety of silicone resins. Desirably the alkyl halide reactant is previously heated and gasified before it is fed into the reactor. The alkyl halide gas may be used alone or in admixture with an inert gas. The feed amount of alkyl halide gas is calculated as an amount (combined with the inert gas) necessary to fluidize the contact mass and hence, properly determined from the diameter of a reactor used and a superficial gas velocity in a column.

In the step of heating the contact mass or imparting catalytic activity to the contact mass, an inert gas is used for fluidizing the contact mass in the reactor. The inert gas used herein includes argon and nitrogen, with the nitrogen being preferred for economy. The flow velocity of inert gas may be at least the velocity at which the contact mass starts fluidizing, especially about 5 times the fluidization starting velocity. If the flow velocity of inert gas is below this range, uniform fluidization of the contact mass would be difficult. If the flow velocity of inert gas is beyond this range, more metallic silicon powder would scatter and the losses of inert gas and heat would increase. It is preferred to flow the inert gas in a circulating manner.

After the contact mass is given catalytic activity as mentioned above, the alkyl halide is introduced into the reactor whereby gas-solid contact reaction takes place between the alkyl halide and metallic silicon to form an alkylhalosilane. The conditions of this gas-solid contact reaction may be the same as in conventional processes. For example, the reaction temperature is 280 to 300° C. With respect to the reaction mode, it is possible to effect reaction in a fluidized layer under continuous conditions, in an agitated layer, or in a fixed layer.

EXAMPLE

Examples of the present invention are given below by way of illustration and not by way of limitation. All parts are by weight.

Examples 1–2

A fluidized bed reactor of carbon steel having a diameter of 50 mm and a height of 300 mm was charged with 100 parts of metallic silicon powder and 4 parts of a catalyst mixture comprising metallic copper powder. The boron compound shown in Table 1 was also loaded in a varying amount.

Thereafter, methyl chloride was admitted into the reactor at a flow velocity of 1.3 cm/sec. and the temperature within the reactor was increased to 330° C. for reaction to continue. Reaction was terminated after 6 hours. Table 1 shows the accumulative STY from the start to the end of reaction. STY representative of a rate of formation of alkylhalosilane is equal to [the weight (g) of alkylhalosilanes]/[the weight (kg) of metallic silicon×time (hr)].

Table 1 also reports the proportion of dimethyldichlorosilane (D), the proportion of methyldichlorosilane (H), and the proportion of high-boiling products (R) relative to the entire amount of methylchlorosilanes produced. Note that the high-boiling products are those products having a boiling point of higher than 70° C. under atmospheric pressure, such as hydrosilanes and disilanes in the methylchlorosilanes produced.

TABLE 1

|  | E1 | E2 |
| --- | --- | --- |
| Boron compound | BPO$_4$ | BPO$_4$ |
| B in contact mass (ppm) | 1000 | 4000 |
| STY (g/kg · hr) | 131.1 | 135.1 |
| D (wt %) | 88.5 | 88.4 |
| H (wt %) | 2.03 | 2.17 |
| R (wt %) | 3.11 | 3.90 |

Example 3

A fluidized bed reactor of carbon steel having a diameter of 50 mm and a height of 300 mm was charged with 100 parts of metallic silicon powder containing 7.0 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction was terminated after 6 hours. Table 2 shows the accumulative STY from the start to the end of reaction. Table 2 also reports the proportion of dimethyldichlorosilane (D), the proportion of methyldichlorosilane (H) and the proportion of high-boiling products (R) relative to the entire amount of methylchlorosilanes produced.

Example 4

A fluidized bed reactor of carbon steel having a diameter of 50 mm and a height of 300 mm was charged with 100 parts of metallic silicon powder containing 74 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction was terminated after 6 hours. Table 2 shows the accumulative STY from the start to the end of reaction as well as the proportions of D, H and R.

Example 5

A fluidized bed reactor of carbon steel having a diameter of 50 mm and a height of 300 mm was charged with 100 parts of metallic silicon powder containing 148 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction was terminated after 6 hours. Table 2 shows the accumulative STY from the start to the end of reaction as well as the proportions of D, H and R.

Example 6

A fluidized bed reactor of carbon steel having a diameter of 50 mm and a height of 300 mm was charged with 100 parts of metallic silicon powder containing 2200 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction w as terminated after 6 hours. Table 2 shows the accumulative STY from the start to the end of reaction as well as the proportions of D, H and R.

Comparative Example 1

A fluidized bed reactor of carbon steel having a diameter of 50 mm and a height of 300 mm was charged with 100 parts of metallic silicon powder containing 0.032 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction was terminated after 6 hours. Table 2 shows the accumulative STY from the start to the end of reaction as well as the proportions of D, H and R.

Comparative Example 2

A fluidized bed reactor of carbon steel having a diameter of 50 mm and a height of 300 mm was charged with 100 parts of metallic silicon powder containing 0.50 ppm of boron and 4 parts of a catalyst mixture comprising metallic copper powder. The boron concentration in the contact mass is shown in Table 2.

Thereafter, methyl chloride was admitted into the reactor at a flow velocity of 1.3 cm/sec. and the temperature within the reactor was increased to 330° C. for reaction to continue. Reaction was terminated after 6 hours. Table 2 shows the accumulative STY from the start to the end of reaction as well as the proportions of D, H and R.

In Examples 3–6 and Comparative Examples 1–2, the predetermined amounts of boron were contained in the metallic silicon powder using boric acid, a metal borate (wherein the metal is sodium or potassium) or boron oxide. The boron compound was added prior to reducing reaction in a process of refining silicon raw material. More particularly, silica rock, char coal, wood pieces were admitted into an electric furnace together with the boron compound. Thereafter, an arc was generated above 1,500° C. to effect reducing reaction. The product was transferred to a container where nitrogen and air were bubbled for 1 to 20 hours. After oxide slug was removed, the end powder was cooled.

TABLE 2

|  | E3 | E4 | E5 | E6 | CE1 | CE2 |
|---|---|---|---|---|---|---|
| B in contact mass (ppm) | 6.7 | 71.2 | 142 | 2115 | 0.031 | 0.48 |
| STY (g/kg · hr) | 101.6 | 102.8 | 111.6 | 110.5 | 80.1 | 83.5 |
| D (wt %) | 88.3 | 88.9 | 89.0 | 88.7 | 87.4 | 86.9 |
| H (wt %) | 1.88 | 1.81 | 1.94 | 1.81 | 2.87 | 2.90 |
| R (wt %) | 2.10 | 2.50 | 2.51 | 2.05 | 2.16 | 2.50 |

Example 7

A fluidized bed reactor of carbon steel having a diameter of 50 mm and a height of 300 mm was charged with 100 parts of metallic silicon powder containing 7.0 ppm of boron, 3.7 parts of metallic copper powder, and 0.3 part of metallic copper powder containing 2.0% by weight of boron. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

Example 8

A fluidized bed reactor of carbon steel having a diameter of 50 mm and a height of 300 mm was charged with 100 parts of metallic silicon powder containing 550 ppm of boron, 3.5 parts of metallic copper powder, and 0.5 part of metallic copper powder containing 2.0% by weight of boron. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

Example 9

A fluidized bed reactor of carbon steel having a diameter of 50 mm and a height of 300 mm was charged with 100 parts of metallic silicon powder containing 148 ppm of boron, 4.0 parts of metallic copper powder, and 1.2 parts of titanium boride. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

Example 10

A fluidized bed reactor of carbon steel having a diameter of 50 mm and a height of 300 mm was charged with 100 parts of metallic silicon powder containing 550 ppm of boron, 4.0 parts of metallic copper powder, and 0.5 part of zirconium boride. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

Example 11

A fluidized bed reactor of carbon steel having a diameter of 50 mm and a height of 300 mm was charged with 100 parts of metallic silicon powder containing 74 ppm of boron, 4.0 parts of metallic copper powder, and 0.5 part of niobium boride. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

Example 12

A fluidized bed reactor of carbon steel having a diameter of 50 mm and a height of 300 mm was charged with 100 parts of metallic silicon powder containing 148 ppm of boron, 3.5 parts of metallic copper powder, and 1.0 part of tungsten boride. The boron concentration in the contact mass is shown in Table 3.

Thereafter, methyl chloride was admitted into the reactor at a flow velocity of 1.3 cm/sec. and the temperature within the reactor was increased to 330° C. for reaction to continue. Reaction was terminated after 6 hours. Table 3 shows the accumulative STY from the start to the end of reaction as well as the proportions of D, H and R.

It is noted that the metallic silicon powders containing 7 to 550 ppm of boron used in Examples 7–12 were prepared as in Example 3–6. The metallic copper powder containing 2.0% by weight of boron was prepared by mixing boron and copper powders, heating the mixture in a nitrogen atmosphere over 2 hours from room temperature to a high temperature of 1,800 to 2,200° C., holding the melt at the high temperature for 1 hour, and cooling the melt.

TABLE 3

| Boride | Example | | | | | |
|---|---|---|---|---|---|---|
| | 7 copper boride | 8 copper boride | 9 titanium boride | 10 zirconium boride | 11 niobium boride | 12 tungsten boride |
| B in contact mass (ppm) | 55 | 625 | 3690 | 1443 | 974 | 1362 |
| STY (g/kg · hr) | 119.2 | 125.8 | 116.6 | 120.4 | 121.5 | 120.5 |
| D (wt %) | 88.7 | 89.1 | 90.0 | 89.1 | 89.3 | 89.3 |
| H (wt %) | 2.10 | 2.29 | 1.94 | 1.98 | 2.87 | 2.90 |
| R (wt %) | 2.11 | 2.09 | 2.01 | 2.31 | 2.05 | 2.13 |

Example 13

A fluidized bed reactor of carbon steel having a diameter of 50 mm and a height of 300 mm was charged with 100 parts of metallic silicon powder containing 7.0 ppm of boron, 4 parts of a catalyst mixture comprising metallic copper powder, and 0.2 part of boron nitride. The boron concentration in the contact mass is shown in Table 4.

Thereafter, methyl chloride was admitted into the reactor at a flow velocity of 1.3 cm/sec. and the temperature within the reactor was increased to 330° C. for reaction to continue. Reaction was terminated after 6 hours. Table 4 shows the accumulative STY from the start to the end of reaction as well as the proportions of D, H and R.

Example 14

A fluidized bed reactor of carbon steel having a diameter of 50 mm and a height of 300 mm was charged with 100 parts of metallic silicon powder containing 7.0 ppm of boron, 4 parts of a catalyst mixture comprising metallic copper powder, and 0.7 part of boron nitride. The boron concentration in the contact mass is shown in Table 4.

Thereafter, methyl chloride was admitted into the reactor at a flow velocity of 1.3 cm/sec. and the temperature within the reactor was increased to 330° C. for reaction to continue. Reaction was terminated after 6 hours. Table 4 shows the accumulative STY from the start to the end of reaction as well as the proportions of D, H and R.

Example 15

A fluidized bed reactor of carbon steel having a diameter of 50 mm and a height of 300 mm was charged with 100 parts of metallic silicon powder containing 7.0 ppm of boron, 4 parts of a catalyst mixture comprising metallic copper powder, and 1.4 parts of boron nitride. The boron concentration in the contact mass is shown in Table 4.

Thereafter, methyl chloride was admitted into the reactor at a flow velocity of 1.3 cm/sec. and the temperature within the reactor was increased to 330° C. for reaction to continue. Reaction was terminated after 6 hours. Table 4 shows the accumulative STY from the start to the end of reaction as well as the proportions of D, H and R.

Example 16

A fluidized bed reactor of carbon steel having a diameter of 50 mm and a height of 300 mm was charged with 100 parts of metallic silicon powder containing 7.0 ppm of boron, 4 parts of a catalyst mixture comprising metallic copper powder, and 0.5 part of boron carbide. The boron concentration in the contact mass is shown in Table 4.

Thereafter, methyl chloride was admitted into the reactor at a flow velocity of 1.3 cm/sec. and the temperature within the reactor was increased to 330° C. for reaction to continue. Reaction was terminated after 6 hours. Table 4 shows the accumulative STY from the start to the end of reaction as well as the proportions of D, H and R.

Example 17

A fluidized bed reactor of carbon steel having a diameter of 50 mm and a height of 300 mm was charged with 100 parts of metallic silicon powder containing 78 ppm of boron, 4 parts of a catalyst mixture comprising metallic copper powder, and 3.0 parts of boron metaphosphate. The boron concentration in the contact mass is shown in Table 4.

Thereafter, methyl chloride was admitted into the reactor at a flow velocity of 1.3 cm/sec. and the temperature within the reactor was increased to 330° C. for reaction to continue. Reaction was terminated after 6 hours. Table 4 shows the accumulative STY from the start to the end of reaction as well as the proportions of D, H and R.

TABLE 4

| Boron compound | Example | | | | |
|---|---|---|---|---|---|
| | 13 boron nitride | 14 boron nitride | 15 boron nitride | 16 boron carbide | 17 boron metaphosphate |
| B in contact mass (ppm) | 843 | 2919 | 5793 | 3751 | 1001 |
| STY (g/kg · hr) | 123.2 | 119.8 | 111.6 | 110.7 | 121.0 |
| D (wt %) | 89.0 | 90.6 | 89.0 | 88.8 | 88.5 |
| H (wt %) | 1.83 | 1.77 | 1.94 | 1.85 | 2.87 |
| R (wt %) | 1.55 | 1.44 | 1.47 | 2.00 | 2.57 |

By the inexpensive means of adding an effective amount of boron to a conventional contact mass in a process for preparing alkylhalosilane by direct synthesis, the invention is successful in increasing the amount of dialkyldihalosilane produced in a desired STY while minimizing the amount of unnecessary hydrosilanes and disilanes. The productivity of a process for preparing alkylhalosilane by direct synthesis is significantly improved.

Although some preferred embodiments have been described, many modifications and variations may be made thereto in-the light of the above teachings. It is therefore to be understood that within the scope of the appended claims, the invention may be practiced otherwise than as specifically described.

We claim:

1. A process for preparing an alkylhalosilane of general formula (1):

$$R_nSiX_{4-n} \qquad (1)$$

wherein R is alkyl having 1 to 4 carbon atoms, X is halogen atom, and n is an integer of 0 to 4, comprising charging a reactor with a contact mass comprising a metallic silicon powder and a copper catalyst, the contact mass containing 1 to 10,000 ppm by weight of elemental boron, and feeding a reactant gas containing an alkyl halide into the reactor whereby the silane is formed by direct synthesis.

2. The process of claim 1 wherein the contact mass contains 50 to 10,000 ppm of elemental boron.

3. The process of claim 1 wherein the contact mass has been formed by using a metallic silicon powder containing boron and/or adding boron or a boron compound.

4. The process of claim 1 wherein said metallic silicon has a purity of at least 98% by weight.

5. The process of claim 1 wherein said metallic silicon powder is in the form of particles having a particle size of 5 to 150 μm.

6. The process of claim 1 wherein the weight/weight ratio of said copper catalyst to said metallic silicon powder is 2 to 8:100.

7. The process of claim 2 wherein said contact mass contains 55 to 6,000 ppm of elemental boron.

8. The process of claim 7 wherein said contact mass contains 200 to 5,000 ppm of elemental boron.

9. The process of claim 3 wherein said metallic silicon powder containing boron is made by adding a non-volatile boron compound to silicon in a molten state, wherein said boron compound is a naturally occurring mineral containing boron; a boride of formula $M^1_2B$, wherein $M^1$ is Fe, Co, Ni, Mn, Mo, W or Ta; a boride of formula $M^2_3B_2$, wherein $M^2$ is Mg; a boride of formula $M_3B$, wherein $M^3$ is Fe, Co, Ni, Mn, Cr, Mo, W, Nb or Ta; a boride of formula $M^4_3B_4$, wherein $M^4$ is Ta, Nb, Mn or Cr; a boride of formula $M^5B_2$, wherein $M^5$ is Ti, Zr, Hf, V, Nb, Ta or Cr; a boride of formula $M^6_2B_5$, wherein $M^6$ is Mo or W; or boron nitride, boron carbide, boron phosphide or boron phosphate.

10. The process of claim 9, wherein said naturally occurring mineral containing boron is borax, kernite or colemanite.

11. The process of claim 3 wherein said metallic silicon powder containing boron is made under silicon refining conditions wherein a boron compound selected from boric acid, metal borate or boron oxide is reduced.

12. The process of claim 3, wherein said metallic silicon powder containing boron is made by refining into silicon a raw material which is boron-containing quartz, boron-containing coal, boron-containing coke, boron-containing char coal or boron-containing eucalyptus.

13. The process of claim 3, wherein the boron compound is added to said contact mass during the direct synthesis and said boron compound is elemental boron; a boron-copper alloy; a boride of formula $M^1_2B$, wherein $M^1$ is Fe, Co, Ni, Mn, Mo, W or Ta; a boride of formula $M^2_3B_2$, wherein $M^2$ is Mg; a boride of formula $M_3B$, wherein $M^3$ is Fe, Co, Ni, Mn, Cr, Mo, W, Nb or Ta; a boride of formula $M^4_3B_4$, wherein $M^4$ is Ta, Nb, Mn or Cr; a boride of formula $M^5B_2$, wherein $M^5$ is Ti, Zr, Hf, V, Nb, Ta or Cr; a boride of formula $M^6_2B_5$, wherein $M^6$ is Mo or W; or boron nitride, boron carbide, boron phosphide or boron phosphate.

14. The process of claim 13, wherein said boron compound is heated to about 200° C. before it is added to said reactor.

15. The process of claim 1, wherein said alkyl halide is methyl chloride.

16. The process of claim 1, wherein said alkyl halide is heated and gasified before it is fed into said reactor.

17. The process of claim 3, wherein the contact mass is formed using a metallic silicon having a high boron concentration.

* * * * *